United States Patent [19]

Rossi, Jr. et al.

[11] Patent Number: 5,658,796

[45] Date of Patent: Aug. 19, 1997

[54] OPTICAL RESOLUTION OF ALKYL CHROMAN-2-CARBOXYLATES

[75] Inventors: Richard F. Rossi, Jr., Norton; Charles M. Zepp, Hardwick; Donald L. Heefner, Hudson, all of Mass.

[73] Assignee: SepraChem, Inc., Marlborough, Mass.

[21] Appl. No.: 475,007

[22] Filed: Jun. 7, 1995

[51] Int. Cl.$^6$ .................................................. C12P 41/00
[52] U.S. Cl. ..................... 435/280; 435/125; 435/881; 549/405
[58] Field of Search ........................... 549/405; 435/125, 435/280, 881

[56] References Cited

U.S. PATENT DOCUMENTS

| | | | |
|---|---|---|---|
| 5,037,747 | 8/1991 | Coffen et al. | 435/125 |
| 5,089,637 | 2/1992 | Urban | 549/407 |
| 5,274,300 | 12/1993 | Dodds et al. | 435/280 |
| 5,371,014 | 12/1994 | Matsuyama et al. | 435/280 |
| 5,374,554 | 12/1994 | Komatsubara et al. | 435/252.3 |
| 5,378,627 | 1/1995 | Shibatani et al. | 435/280 |
| 5,393,664 | 2/1995 | Kira et al. | 435/156 |

FOREIGN PATENT DOCUMENTS

| | | |
|---|---|---|
| 0343714A1 | 11/1989 | European Pat. Off. . |
| 0362556A1 | 4/1990 | European Pat. Off. . |
| 0546388A1 | 6/1993 | European Pat. Off. . |

OTHER PUBLICATIONS

"Quantitative Analyses of Biochemical Kinetic Resolutions of Enantiomers", Chen et al., *J. Am. Chem. Soc.* 104, 7294–7299 (1982).

*Primary Examiner*—Johann Richter
*Assistant Examiner*—Laura L. Stockton
*Attorney, Agent, or Firm*—Heslin & Rothenberg, P.C.

[57] ABSTRACT

Described herein is a process for resolving a racemic (C>3) alkyl (R, S) chroman-2-carboxylate compound useful as intermediates in the synthesis of optically pure pharmaceutical compounds is disclosed. The process utilizes a microbial enzyme derived from *Serratia marcescens* to catalyze the enantioselective hydrolysis of the (C>3) alkyl (S)-chroman-2-carboxylate enantiomer of the racemic mixture to its corresponding carboxylic acid at a faster rate than the R-enantiomer. An enantiomerically pure S-configured carboxylic acid is thereby formed which can undergo acidic esterification to provide an optically pure (C>3) alkyl (S)-chroman-2-carboxylate intermediate for subsequent pharmaceutical synthesis. The nonhydrolyzed (C>3) alkyl (R)-chroman-2-carboxylate enantiomer can also be isolated to provide an optically pure pharmaceutical precursor.

11 Claims, No Drawings

OPTICAL RESOLUTION OF ALKYL CHROMAN-2-CARBOXYLATES

The present invention relates to a process for the resolution of alkyl chroman-2-carboxylates having the general formula (I)

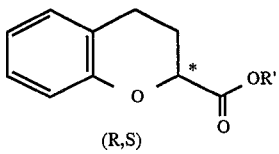

wherein R' is (C>3) alkyl, preferably isobutyl. (Use of an asterisk (*) herein indicates the chiral center.) The invention also relates to the enantioselective enzymatic hydrolysis of one enantiomer in the racemic mixture of such esters by use of a microbial esterase derived from *Serratia marcescens* to form an enantiomerically pure chroman-2-carboxylic acid which can then be converted to a variety of esters, amides, and other derivatives of carboxylic acids.

BACKGROUND OF THE INVENTION

Optically active esters and acids, such as (C>3) alkyl chroman-2-carboxylates and chroman-2-carboxylic acid, having a single chiral center located on the carbon in the 2-position of the chroman structure and adjacent to the carboxyl group are useful as precursors in the chemical synthesis of certain pharmaceutical compounds. For example, compounds of the general formula (II) below, as described in European Patent 0546388 to AG Bayer, provide utility in the treatment of numerous central nervous system and cardiovascular diseases.

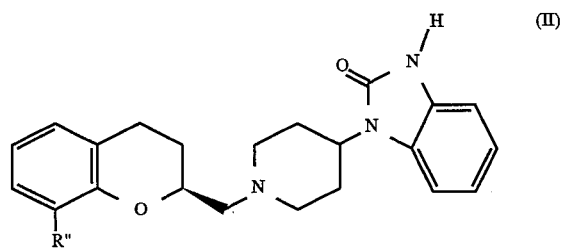

Compounds (II), wherein R" is hydrogen or methoxy, contain a single chiral center at the 2-position of the chroman structure and are synthesized by the reaction of alkyl chroman-2-carboxylate or chroman-2-carboxylic acid precursors in an intermediate step. Alkyl as used herein encompasses linear, branched, and cyclic hydrocarbon residues of 1 to 20 carbons; (C>3) alkyl refers to the subset of alkyl having 4 to 20 carbons.

The administration of an optically pure pharmaceutical compound (II) synthesized from an enantiomer of the (C>3) alkyl chroman-2-carboxylate or chroman-2-carboxylic acid intermediate may provide an improvement over the administration of the racemic compound. Often when administering a racemic compound, one enantiomer may actually provide the beneficial effects while the opposite enantiomer may be deleterious or inert. Thus, advantages associated with the administration of the racemic mixture may be retained by using a single enantiomer of the compound without accompanying adverse side effects. Resolution of the racemic (R, S)-carboxylate or acid intermediate into its individual enantiomers is a convenient point in the overall synthetic route to the corresponding optically pure pharmaceutical compounds (II) at which to introduce desired stereochemistry.

Therefore, separation of the enantiomers is desirable, and a need exists for a convenient and economic method for producing the enantiomers which can be performed on a commercial scale. Resolution of the racemic carboxylate mixture into isolated enantiomers provides such a method and permits large-scale syntheses of the individual enantiomers.

Resolution of racemic mixtures of chiral compounds can often be achieved by subjecting the racemates to the stereoselective action of various enzymes. Generally, enzymes for use in resolutions should exhibit a high degree of stereoselectivity for catalyzing the reaction of one isomer to the exclusion of others. Enzymatic resolution by enantioselective hydrolysis of various ester compounds has been widely employed for the lab-scale, preparative-scale, and industrial-scale production of many optically pure acids and esters.

One class of enzymes, the hydrolases, which includes lipases, proteases, and esterases, for example, is often used in the resolution of enantiomers because they are commercially available at reasonable cost, they do not require expensive cofactors, and some exhibit reasonable tolerance to organic solvents. Additionally, hydrolases are known to stereoselectively catalyze the hydrolysis of certain carboxylic acid derivatives, including esters.

For example, Urban (U.S. Pat. No. 5,089,637) employed enzymatic hydrolysis using a microbial esterase derived from *Pseudomonas fluorescens* to resolve racemic mixtures of ($C_1$–$C_3$) alkyl chroman-2-carboxylates. The esterase catalyzes stereoselective hydrolysis of the S-carboxylate enantiomer to produce a mixture of optically pure ($C_1$–$C_3$) alkyl (R)-chroman-2-carboxylate and (S)-chroman-2-carboxylic acid.

However, resolution of the enantiomers of (C>3) alkyl chroman-2-carboxylates by stereoselective enzymatic hydrolysis has not heretofore been described. Such a resolution is desirable in order to provide optically pure (C>3) alkyl chroman-2-carboxylates and corresponding acids for use as synthetic precursors in the manufacture of optically pure pharmaceutical compounds (II) having the desired R- or S- stereochemistry.

Therefore, a need exists for an inexpensive and efficient method for producing on a commercial scale the individual enantiomers of (C>3) alkyl chroman-2-carboxylates and chroman-2-carboxylic acid.

SUMMARY OF THE INVENTION

As a result of various studies, it has now been unexpectedly found that optically pure (C>3) alkyl chroman-2-carboxylates can be conveniently prepared in high enantiomeric purity by esterase catalyzed hydrolysis of the corresponding racemic ester compound. The resolution process of the present invention is accomplished through the use of a microbial esterase derived from *Serratia marcescens* that stereoselectively catalyzes hydrolysis of the S-ester at a faster rate than the R-ester. Optically pure (S)-chroman-2-carboxylic acid is produced while the corresponding (C>3) alkyl (R)-chroman-2-carboxylate enantiomer remains as the ester.

Recovery of the latter species in optically purified form is thereafter possible permitting its use as an intermediate in the production of pharmaceutical compounds having an absolute R-configuration. Likewise, isolation of the hydrolyzed S-enantiomer followed by esterification provides the oppositely configured S-ester. Finally, racemization of either isolated ester can be performed.

In accordance with the present invention, a method is therefore provided for resolving a racemic mixture of (C>3) alkyl chroman-2-carboxylates, which comprises the steps of:

(a) providing an organic phase comprising a mixture of (C>3) alkyl chroman-2-carboxylate enantiomers represented by formula (I)

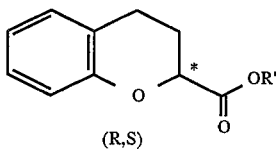

wherein R' is (C>3) alkyl;

b) contacting said organic phase with an aqueous solution comprising water and a catalytic amount of a microbial esterase derived from *Serratia marcescens* to form a mixture comprising (C>3) alkyl (R)-chroman-2-carboxylate and (S)-chroman-2-carboxylic acid;

c) separating said (S)-chroman-2-carboxylic acid from said (C>3) alkyl (R)-chroman-2-carboxylate; and d) recovering said (C>3) alkyl (R)-chroman-2-carboxylate.

The chroman ring system is known in Chemical Abstracts nomenclature as (2H)-3,4-dihydro-1-benzopyran.

Steps (a) and (b) are depicted as follows:

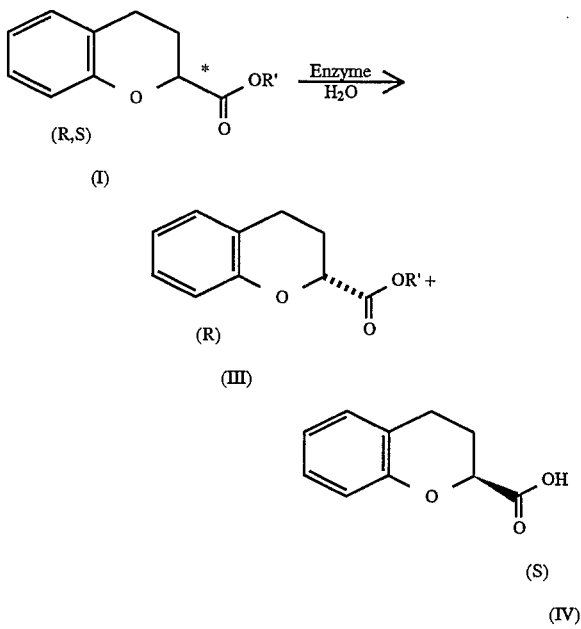

The S-configured carboxylic acid enantiomer represented as formula (IV) above can then be esterified to form an optically pure (C>3) alkyl (S)-chroman-2-carboxylate. The (C>3) alkyl (R)-chroman-2-carboxylate enantiomer represented as formula (III) above of the racemic mixture remains substantially unaffected by the hydrolysis and can be isolated from the organic solution as the absolutely configured, optically pure (C>3) alkyl (R)-chroman-2-carboxylate enantiomer (III).

The esterase derived from *Serratia marcescens* is water soluble, whereas the esters of the present invention exhibit very low solubilities in water. Therefore, the enzyme-mediated optical resolution may be conducted under two-phase or multiphase reaction conditions.

In a preferred embodiment, the R' alkyl group of the racemate is isobutyl. Racemic isobutyl chroman-2-carboxylate is shown as formula (V).

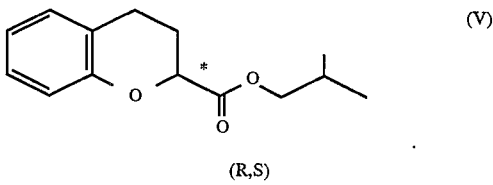

Stereospecific hydrolysis of the S-enantiomer in the racemic carboxylate mixture provides isobutyl (R)-chroman-2-carboxylate.

DETAILED DESCRIPTION OF THE INVENTION

The present invention provides a method for the production of resolved (C>3) alkyl chroman-2-carboxylates, subsequently useful as intermediates in the synthesis of optically pure pharmaceutical compounds (II). Specifically, this invention relates to the production of optically pure pharmaceutical intermediates by enzymatic resolution of racemic mixtures of (C>3) alkyl chroman-2-carboxylates (I) using a resolution process in which the racemate is contacted with an esterase derived from *Serratia marcescens*. The (C>3) alkyl (S)-chroman-2-carboxylate enantiomer is preferentially hydrolyzed and removed from the R-enantiomer, thus producing the enantiomerically enriched (C>3) alkyl (R)-chroman-2-carboxylate (III) and enantiomerically enriched (S)-chroman-2-carboxylic acid (IV).

The carboxylic acid is easily separated from the remaining R-ester, due to their differential solubilities in organic solvents, by known methods. In the present invention, by virtue of the lipophilicity of (C>3) alkyl esters, all the chroman esters are soluble in a variety of organic solvents that are immiscible with water, while the enantiomerically enriched (S)-chroman-2-carboxylic acid product of the hydrolysis is soluble in water at the appropriate pH. (The term "immiscible" as used herein refers to liquids that cannot be uniformly mixed in all solvents which are completely, substantially, or proportions, and "immiscible with water" includes partially immiscible with water—i.e. solvents such as butanol that form a separate organic phase when placed in contact with water.)

The resolution process described herein is a kinetic resolution process in which each enantiomer of the racemic substrate mixture exhibits some susceptibility to enzymatic hydrolysis, but the S-enantiomer is hydrolyzed more rapidly than the R-enantiomer.

The ability of an enzyme to discriminate between two competitively reacting enantiomers may be quantified by the enantioselectivity value E, as described by C. S. Chen et al. (J. Amer. Chem. Soc., 104 (1982) 7294). The formula for calculation of E in the case of a subtractive kinetic resolution process is given as follows:

$$E=\{\ln[(1-x)(1-ee(S))]/\ln[(1-x)(1+ee(S))]\}$$

where x is the degree of conversion of the entire quantity of starting substrate, expressed as a decimal fraction, and ee(S) is the enantiomeric excess of the remaining, non-hydrolyzed substrate enantiomer, also expressed as a decimal fraction. This formula permits comparison of enzyme reactions which have proceeded to different degrees of conversion, in which case direct comparison of the enantiomeric excess of the remaining carboxylate substrate is not possible. It is also possible to use this E value and corresponding calculations to compare the apparent selectivity of the same enzyme operating under varying conditions.

In the resolution process of the present invention, an infinitely large E value displayed by the enzyme would be ideal. If E=∞ and 50% of the total starting substrate has been hydrolyzed, then 100% of the non-hydrolyzed material will remain in the organic phase after reaction at an optical purity of 100% enantiomeric excess. However, if the enzyme displays a lower E value, the overall extent of hydrolysis must be allowed to proceed past 50%, to an extent that is determined by the formula derived by Chen et al. and reproduced above. Generally, an E value of at least 25 is necessary for a process to be of commercial value. In the present invention, the enzyme catalyst derived from *Serratia marcescens* has been surprisingly found to be S-selective with a relatively large E value.

Because the (C>3) alkyl chroman-2-carboxylate racemic mixture (I) is available at room temperature as a liquid that emulsifies into a second (organic) phase upon addition of an aqueous solution, the racemic mixture may be used in the present invention without addition of an organic solvent. Alternatively, racemic (C>3) alkyl chroman-2-carboxylate (I) may be dissolved in an organic solvent to form an organic phase which is separable from aqueous solution. The selected organic solvent is one which is appreciably immiscible with water, such as hexane, heptane, methyl isobutyl ketone, t-butyl methyl ether, toluene, ethyl acetate, or methylene chloride. However, the invention is not limited to the use of the above-mentioned solvents, and other suitable water immiscible organic solvents that may be used will be obvious to those skilled in the art.

The enzyme catalyst derived from *Serratia marcescens* for use in the present invention may be obtained in aqueous solution. Alternatively, the esterase may be obtained in powdered form and subsequently dissolved in water. While highly purified enzyme preparations are not necessary for the process of this invention, if the enzyme to be used herein has intrinsically low specific activity units (units of catalytic activity per weight of protein), crude preparations thereof can cause practical problems by requiring unnecessarily large volumes of reaction mixtures and correspondingly large reactor volumes.

Sources and cultivation of *Serratia marcescens* are disclosed in U.S. Pat. No. 5,378,627 to Shibatani et al., U.S. Pat. No. 5,374,554 to Kamatsubara et al., U.S. Pat. No. 5,371,014 to Matsuyama et al., and U.S. Pat. No. 5,393,664 to Kira et al. Microorganisms having IFO numbers assigned thereto, such as *Serratia marcescens* IFO3046, for example, are described in the List of Culture, 8th ed., vol. 1 (1988) published by the Institute for Fermentation, Osaka (IFO) and available therefrom. *Serratia marcescens* ATCC14226 is described in the Catalogue of Bacteria phages rDNA Vectors, 16th ed. (1985) published by American Type Culture Collection (ATCC) and available therefrom.

Briefly, *Serratia marcescens* produces an esterase that may be obtained by extraction from cultured broths of the microorganisms, followed by purifying the extract by a conventional method. In addition, the bacteria may be either wild type or mutants. Recombinant strains derived using genetic means such as cell fusion or genetic engineering may also be used. The medium for cultivating *Serratia marcescens* for use in the present invention may be any medium on which the microorganisms will grow. For example, an ordinary liquid nutrient medium containing carbon sources, nitrogen sources, inorganic salts and organic nutrients can be used.

The concentration of the (C>3) alkyl chroman-2-carboxylate compound (I) to be hydrolyzed is not critical. Similarly, the concentration of the esterase required to effect hydrolysis of the S-carboxylate is not critical to the practice of this invention. However, in preferred embodiments, the enzyme concentration will be an amount which is effective to achieve hydrolysis in a reasonable period of time and may depend on the purity of the enzyme.

In the two-phase hydrolysis system, the preferred pH range of the aqueous phase is about 5.0 to 9.75 which covers the pH optimum for the *Serratia marcescens* preparation in use. It is desirable to maintain the pH of the aqueous phase within the desired range over the course of the hydrolysis by use of a buffer system. Examples of buffers with buffering capacity over the desired range include, but are not limited to, carbonates, bicarbonates, phosphates, borates, and citrates. Additionally, an automatic titrator using NaOH as the titrant, for example, or other pH controlling device may be used.

Similarly, the temperature at which the hydrolysis is performed may vary over a wide range, preferably between about 10°–45° C., provided that both the aqueous and organic phases remain liquid, the enzyme does not experience denaturation at a rate too rapid to allow its use, and the carboxylates remain stable. The relative volumes of the aqueous and organic phases are not critical, and may vary over a wide range. In the preferred embodiment of the present invention, the temperature, the pH of the aqueous phase, the concentration of the enzyme (*Serratia marcescens*) in the aqueous phase, and the concentration of the (C>3) alkyl (R, S)-chroman-2-carboxylate racemic mixture are chosen such that an optimal combination of rate and enantioselectivity of hydrolysis is realized.

The esterase-catalyzed hydrolysis reaction is conducted by contacting the racemic carboxylate-containing organic phase with the aqueous phase in the presence of the *Serratia marcescens* esterase using conventional stirring or shaking techniques. Alternatively, known methods wherein the enzymatic resolution process is conducted within a multi-phase/extractive enzyme membrane reactor may be employed. An example of such a membrane reactor may be found in U.S. Pat. No. 5,077,217 (Matson et al.), the disclosure of which is incorporated by reference.

Since the (C>3) alkyl chroman-2-carboxylate is preferentially soluble in the organic phase, the R ester will remain in the organic phase after hydrolysis, and the enantiomeric ester excess (ee Ester) in the organic phase will increase as a function of the extent of hydrolysis and enantioselectivity value E. Likewise, after hydrolysis, the aqueous solution will contain an S-acid and has an enantiomeric acid excess (ee Acid) greater than 0. The extent of hydrolysis of the total racemic (C>3) alkyl chroman-2-carboxylate substrate (I) may be adjusted to permit the recovery of the unreacted R-ester at any desired level of enantiomeric excess; higher conversions yield organic-phase R-esters of increasing optical purity.

The progress of the esterase-catalyzed hydrolysis may be conveniently monitored by periodic HPLC analyses of the reaction mixture until the desired extent of conversion is reached. After completion of the hydrolysis, the optically pure S-acid enantiomer is then separated from the oppositely configured R-carboxylate enantiomer, preferably by separating the aqueous and organic phases. Common methods of separation include, but are not limited to, gravitational settling and centrifugation. Generally, after gravitational settling the aqueous layer can be drained through a tap in the bottom of the reaction vessel.

The substantially optically pure R-ester contained in the organic solution may then be isolated by concentrating the organic layer under reduced pressure. Likewise, the S-carboxylic acid enantiomer produced in the aqueous layer can be isolated by precipitation and filtration, for example. Acid catalyzed esterification of the isolated S-carboxylic acid may then be performed to obtain the S-carboxylate ester. Therefore, according to the present invention, both enantiomers, R and S, of the racemic (C>3) alkyl chroman-2-carboxylate compound (I) or the corresponding carboxylic acid can be resolved and isolated for subsequent use as intermediates in the syntheses of optically pure pharmaceutical compounds.

Racemization of either the isolated R- or S-ester may then be done by refluxing the enantiomer with a base (about 1 mole %) such as potassium-tert-butoxide or sodium-isobutoxide until completion. Other bases including tertiary amines such as triethylamine or strong basic amines such as 1,5-diazabicyclo[4.3.0]non-5-ene or 1,8-diazabicyclo[5.4.0]undec-7-ene may be used to effect racemization. Also, refluxing with sodium or potassium hydroxide in catalytic amounts will cause racemization, although with a concomitant loss of ester due to hydrolysis. However, the invention is not limited to refluxing the isolated enantiomer with the aforementioned bases, and other bases that will effect racemization may be used and will be obvious to those skilled in the art. Racemization may be followed by HPLC or by optical rotation to determine the extent of racemization.

The present invention is more particularly described and explained by means of the following detailed Examples of preferred embodiments. It is to be understood, however, that such Examples are for illustration purposes only and are not intended to limit the scope of the present invention.

EXAMPLE 1

An organic solution was formed containing 40.4 g of a racemic mixture of the isobutyl chroman-2-carboxylate enantiomers dissolved in 100 mL t-butyl methyl ether. The esterase derived from *Serratia marcescens* was obtained from Tanabe Seiyaku Co., Ltd. in an aqueous solution having an enzymatic activity of 5200 units/mL. 5.0 mL of the esterase solution was added to 250 mL of a 0.1M sodium phosphate buffered aqueous solution. The pH was maintained at 8.25 by an automatic titrator using a 2.5M NaOH solution as the titrant. The organic and aqueous solutions were vigorously stirred with a stir plate for 2.5 hours, and samples were analyzed by HPLC after 1 hour and after 2.5 hours. The reaction was then allowed to phase separate, and the aqueous layer was drained. The organic phase was dried over anhydrous sodium sulfate and evaporated to yield the final product. Isobutyl (R)-chroman-2-carboxylate was recovered in an amount of 19.2 g, or a yield of 96.0% The ee(Ester) value was 99.1% after 2.5 hours.

Optical purity of the enantiomers was analyzed by HPLC using a Chiralcel™ OD-R column with a 1:1 acetonitrile/buffer as the mobile phase. The buffer was 7 g sodium perchlorate/liter $H_2O$, adjusted to pH of 2.0 with conc. HCl.

The results of the hydrolysis are summarized in the following TABLE.

TABLE

| Time (hr) | eeAcid (%) | eeEster (%) | Conversion (%) | E | Rate (mmol/hr/mlenz) |
| --- | --- | --- | --- | --- | --- |
| 1 | 93.2 | 84.4 | 47.7 | 77 | 16.9 |
| 2.5 | 94.0 | 99.1 | 51.3 | 173 | 7.3 |

The aqueous phase of the hydrolysis reaction was acidified to pH of 2.0 with conc. HCl forming a white precipitate of (S)-chroman-2-carboxylic acid. The S-acid was extracted into toluene, and the phases were separated. The organic layer was placed in a vessel suitable for acid catalyzed esterification. Sulfuric acid was added to the vessel, and the mixture was heated to reflux. Water was removed by azeotropic distillation. The conversion of the acid to the ester was followed by GC analysis. Isobutyl (S)-chroman-2-carboxylate was thereby formed. Upon completion of the esterification, the sulfuric acid catalyst used in the reaction was removed by washing the reaction product with saturated sodium carbonate, and the S-carboxylate product was azeotropically dried again.

The esterification reaction product containing isobutyl (S)-chroman-2-carboxylate in toluene was then racemized by placing the S-carboxylate in a vessel suitable for refluxing and adding potassium-tert-butoxide (about 1 mole %). The solution was refluxed, and the reaction was followed by HPLC analysis to determine the extent of racemization. When the reaction was complete, the solution was cooled to room temperature and washed with dilute sodium carbonate. Toluene and water were removed by distillation leaving the racemic isobutyl (R, S)-chroman-2-carboxylate behind. The product was confirmed by HPLC and GC analyses.

EXAMPLE 2

Large-scale enzymatic hydrolysis of racemic isobutyl chroman-2-carboxylate was carried out in three batches in a 200 gallon reactor to produce 100 kg of the unhydrolyzed R-ester. Each batch utilized 67 kg substrate dissolved in 100 liters of heptane or toluene. The aqueous phase comprised 1.67 liters of an enzyme solution derived from *Serratia marcescens* (Tanabe) in 420 liters of a 0.1M sodium phosphate buffer solution adjusted to a pH of 8.25 with 28.6 liters of 5M NaOH. The total volume of the reactants was 615.5 liters such that the reactor was running at about 77% of its volume capacity.

After completion of hydrolysis, approximately 6 hours, the phases were permitted to separate, and the aqueous layer was drained through a bottom tap. The organic phase was then dried over anhydrous sodium sulfate (about 3 kg for 150 liters) and evaporated to yield the final unhydrolyzed isobutyl (R)-chroman-2-carboxylate enantiomer. Optical and chemical analyses of the isolated enantiomer were performed using the chromatographic techniques and conditions listed in EXAMPLE 1.

We claim:

1. A method for resolving a mixture of enantiomers of a (C>3) alkyl chroman-2-carboxylate, said method comprising the steps of:

a) providing an organic phase comprising a mixture of (C>3) alkyl chroman-2-carboxylate enantiomers represented by formula (I)

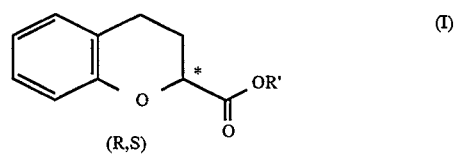

wherein R' is (C>3) alkyl;

b) contacting said organic phase with an aqueous solution comprising water and a catalytic amount of a microbial esterase derived from *Serratia marcescens* to form a mixture comprising (C>3) alkyl (R)-chroman-2-carboxylate and (S)-chroman-2-carboxylic acid;

c) separating said (S)-chroman-2-carboxylic acid from said (C>3) alkyl (R)-chroman-2-carboxylate; and d) recovering said (C>3) alkyl (R)-chroman-2-carboxylate.

2. The method according to claim 1, wherein said organic phase further comprises a water immiscible organic solvent.

3. The method according to claim 1, wherein R' is an isobutyl group.

4. The method according to claim 1, wherein said aqueous solution is maintained at a pH in the range of about 5.0 to 9.75.

5. The method according to claim 1, wherein hydrolysis occurs at a temperature from about 10° C. to about 45° C.

6. The method according to claim 1 further comprising the step of isolating said (S)-chroman-2-carboxylic acid from said aqueous solution.

7. The method according to claim 6 further comprising the step of esterifying said (S)-chroman-2-carboxylic acid to produce (C>3) alkyl (S)-chroman-2-carboxylate.

8. The method according to claim 7, further comprising the step of: refluxing said (C>3) alkyl (S)-chroman-2-carboxylate with a base to produce a mixture of (C>3) alkyl (R, S)-chroman-2-carboxylate enantiomers.

9. The method according to claim 8, wherein said base is selected from the group consisting of potassium-tert-butoxide, sodium-iso-butoxide, potassium hydroxide, sodium hydroxide, triethylamine, 1,5-diazabicyclo[4.3.0]non-5-ene, and 1,8-diazabicyclo[5.4.0]undec-7-ene.

10. The method according to claim 1 further comprising the step of: refluxing said recovered (C>3) alkyl (R)-chroman-2-carboxylate with a base to produce a mixture of (C>3) alkyl (R, S)-chroman-2-carboxylate enantiomers.

11. The method according to claim 10, wherein said base is selected from the group consisting of potassium-tert-butoxide, sodium-iso-butoxide, potassium hydroxide, sodium hydroxide, triethylamine, 1,5-diazabicyclo[4.3.0]non-5-ene, and 1,8-diazabicyclo[5.4.0]undec-7-ene.

* * * * *